United States Patent
Corley et al.

(10) Patent No.: US 7,008,648 B2
(45) Date of Patent: Mar. 7, 2006

(54) PLANT DERIVED OR DERIVABLE MATERIAL WITH APPETITE SUPPRESSING ACTIVITY

(75) Inventors: David Gregory Corley, St. Louis, MO (US); James Miller, St. Louis, MO (US)

(73) Assignee: Novartis Nutrition AG, Berne (CH)

( * ) Notice: Subject to any disclaimer, the term of this patent is extended or adjusted under 35 U.S.C. 154(b) by 541 days.

(21) Appl. No.: 10/287,049

(22) Filed: Nov. 4, 2002

(65) Prior Publication Data

US 2003/0152648 A1     Aug. 14, 2003

Related U.S. Application Data

(60) Provisional application No. 60/332,401, filed on Nov. 16, 2001.

(51) Int. Cl.
*A61K 35/78*    (2006.01)
*A61K 47/00*    (2006.01)
*A01N 43/04*    (2006.01)

(52) U.S. Cl. .................. 424/725; 424/439; 514/33

(58) Field of Classification Search ............... 424/725, 424/439; 514/33
See application file for complete search history.

(56) References Cited

U.S. PATENT DOCUMENTS 6,900,218 B1 *   5/2005   Wang et al. ............. 514/266.1

FOREIGN PATENT DOCUMENTS

| JP | 401026512 A | * | 1/1989 |
| WO | WO 98/46243 | | 10/1998 |

OTHER PUBLICATIONS

Sayed et al., "Pregnane Glycosides From *Stapelia variegata*", Phytochemistry, vol. 39, No. 2, pp. 395-403, (1995).

* cited by examiner

*Primary Examiner*—Susan Coe
*Assistant Examiner*—Randall Winston
(74) *Attorney, Agent, or Firm*—Gary M. Lobel

(57) ABSTRACT

A method of suppressing or curbing appetite and treating or preventing obesity comprising administering to a human or other mammal in need of such treatment an effective amount of plant material derived or derivable from plants of the genera *Stapelia* and *Orbea*.

10 Claims, No Drawings

PLANT DERIVED OR DERIVABLE MATERIAL WITH APPETITE SUPPRESSING ACTIVITY

This application claims the benefit of U.S. Provisional Application No. 60/332,401 filed Nov. 16, 2001, which is hereby incorporated by reference in its entirety.

The present invention relates to plant derived or derivable material with appetite suppressing activity.

Despite a rising worldwide epidemic of obesity there is currently only a very small number of anti-obesity drugs available to manage the problem. Behavioral analysis of pharmacological agent-induced anorexia in animals demonstrates that various compounds profoundly effect feeding behavior in differing ways. This indicates the variety of mechanisms by which pharmacological agents can induce changes in food intake, body weight and eventually body composition. Some of the same pharmacological agents produce decreases in food intake and weight loss in humans. Some of these pharmacological agents do so by modifying the functioning of the appetite system as measured by subjective changes in feelings of hunger and fullness (indices of satiety). Such pharmacological agents can be considered as "appetite suppressants" with clinical potential as anti-obesity agents.

According to the present invention there is provided a method of suppressing or curbing appetite comprising administering to a human or other mammal in need of such treatment an effective amount of plant material derived or derivable from at least one plant of the genera *Stapelia* L. and *Orbea* Haw, hereinafter the plant material of the invention.

The invention further provides the use of plant material derived or derivable from at least one plant of the genera *Stapelia* L. and *Orbea* Haw in the preparation of a pharmaceutical or nutritional formulation for suppressing or curbing appetite.

The invention also provides plant material derived or derivable from at least one plant of the genera *Stapelia* L. and *Orbea* Haw for use as an appetite suppressant or appetite curbing.

Also provided is a method of treating and/or preventing obesity comprising administering to a human or other mammal in need of such treatment an effective amount of plant material derived or derivable from at least one plant of the genera *Stapelia* L. and *Orbea* Haw.

The invention further provides a method of improving the bodily appearance comprising administering to a mammal a plant material derived or derivable from at least one plant of the genera *Stapelia* L. and *Orbea* Haw in an amount effective to curb, reduce or suppress appetite and repeating said administration until a beneficial loss of body weight, e.g., a cosmetically beneficial loss, has occurred.

In another aspect, the invention provides a method for promoting weight loss or maintenance of a desired body weight comprising administering to a human or other mammal in need of such treatment an effective amount of plant material derived or derivable from at least one plant of the genera *Stapelia* L. and *Orbea* Haw.

In a further aspect of the invention, there is provided a use of a composition comprising plant material derived or derivable from at least one plant of the genera *Stapelia* and *Orbea* in the manufacture of a medicament, a pharmaceutical composition or a nutritional composition for suppressing or curbing appetite, for treating and/or preventing obesity, or for promoting weight loss or maintenance of a desired body weight.

The genus *Stapelia* L. comprises some 50 species occurring naturally in tropical and southern Africa and belonging to the family Asclepiadaceae. The genus *Orbea* Haw comprises some 20 species occurring naturally in tropical and southern Africa and also belonging to the family Asclepiadaceae. Preferred *Stapelia* species, which are useful for the purpose of the present invention, include the following: *Stapelia gigantea* L. and *Orbea variegata* (L.) Haw. Synonyms used for *Orbea variegata* L. include *Stapelia variegate* L. and *Stisseria variegata* (L.) Kuntze. Synonyms used for *Stapelia gigantea* are *Stapelia cyclistra, Stapelia marlothii* and *Stapelia nobilis*. Common names of plant species suitable for this invention are Starfish flower, (Giant) Toad Plant, Carrion Plant, etc.

This is the first report of an activity on appetite suppressing, curbing or reducing from plants of the genera *Stapelia* and *Orbea*.

The plant material of the invention may be prepared from the stems and/or roots of the plants used according to the invention, hereinafter referred to as biomass or plant biomass. As used herein, the term "plant material" may refer to one or more of the following: fresh plant material taken directly from the plant without further treatment, dried powder from the original biomass, sap or dried sap, extracts of biomass or fractions thereof, isolated active compounds and synthetic analogues of isolated active compounds. Preferably it refers to the dried sap, extracts or fractions of biomass, isolated active compounds and synthetic analogues thereof.

The plant material may be prepared by one or more of the following processes:

a) by drying and grinding the original biomass to a dried powder;

b) by pressing the plant biomass, collecting the sap and drying the sap;

c) by preparing extracts of the plant biomass with suitable solvents, which may be either used as crude extracts or further fractionated; and d) by isolating pure substances, in particular pregnane glycosides, from the plant biomass.

A suitable method for drying and grinding the original biomass includes either sun drying followed by a heated air-drying or freeze-drying, e.g., lyophilization or chopping of the biomass into small pieces, e.g., 2–10 cm, followed by heated air-drying or freeze-drying. Once sufficient moisture has been removed, e.g., more than 90%, the material can be ground to a coarse particle size, e.g., 0.01–1 mm, using a commercial grinder. For laboratory scale extraction, a coffee grinder or equivalent can be used.

A suitable method for preparing dried sap includes the steps of pressing collected plant biomass to separate the sap from solid plant biomass, recovering the sap free of the solid plant biomass, and either drying the sap or further purifying it, e.g., by way of suitable extraction procedures. The sap may be dried by spray-drying, freeze-drying or vacuum-drying, to form a free-flowing powder.

In general terms, a suitable method for preparing an extract of the biomass of a plant used according to the invention, the extract comprising an appetite suppressing or curbing agent, comprises the steps of treating collected plant biomass, with a solvent to extract a fraction having appetite suppressant or curbing activity, separating the extraction solution from the rest of the plant biomass, removing the solvent from the extraction solution and recovering the extract. The extract so recovered may be further purified by way of suitable extraction or purification procedures.

In a first step, the plant biomass may be ground to a coarse powder or the sap can be dried to yield a powder, as described above. Subsequently a suitable solvent may be added to the powder. Suitable solvents include water, dilute acids, organic solvents, critical, supercritical or near critical fluid solvents, e.g., carbon dioxide, nitrous oxide, propane, ethane, ethylene and fluorohydrocarbons, and mixtures of any of these. Organic solvents may include butane, hexane, acetone, methanol, ethanol, propanol, butanol, methylene chloride, dichloromethane, acetonitrile, ethyl acetate, butyl acetate or any mixture thereof. Alcohol-based solvents, i.e., pure alcohol solvents and mixtures thereof with water or other organic solvents, are preferred. Ethanol is the most preferred solvent for the first extraction step.

The extraction solution may then be separated from the residual plant biomass by an appropriate separation procedure, such as, e.g., filtration and/or centrifugation. The solvent may be removed, e.g., by means of a rotary evaporator. The separated crude extract can then be tested to confirm appetite suppressant or appetite curbing activity in a suitable in vivo bioassay.

In a preferred method, the extract is then further fractionated with dichloromethane:methanol:water, e.g., 5:2:3, in a separatory funnel. The organic phase is removed and dried, then further fractionated by hexane:methanol:water, e.g., 5:4.5:5. The hexane phase is discarded and the aqueous methanolic phase is dried by rotary evaporation to yield a partially purified active extract.

The partially purified active extract may be dissolved in methanol, and may be further fractionated by column chromatography, employing either reversed-phase (C18) or normal phase (silica gel) as an adsorption medium. A plurality of different fractions may be obtained, and each may be evaluated, by suitable bioassaying procedures to determine the appetite suppressing or appetite curbing activity thereof.

In one preferred mode of performing the extraction procedure, a partially purified active extract having appetite suppressant or appetite curbing activity is further fractionated, e.g., by column chromatography using silica gel as an adsorption medium and a 9:1 chloroform:methanol solvent, and the resultant subfractions bioassayed for their appetite suppressant or appetite curbing activity. A sub-fraction displaying appetite suppressant or appetite curbing activity may, if desired, be further fractionated and purified, e.g., conveniently using a column chromatographic procedure, e.g., with silica gel as the adsorption medium and a 9:1 ethylacetate:hexane solvent as eluent. The resultant purified fractions may again be evaluated by suitable bioassay procedures for their appetite suppressant or appetite curbing activity.

Alternatively, the partially-purified extract or fraction can be further fractionated, e.g., by using reversed-phase (C18) HPLC and eluting with water:acetonitrile (70:30) or similar conditions.

The extract may be dried to remove moisture, e.g., by spray-drying, freeze-drying or vacuum-drying, to yield a free-flowing powder. Optionally, the extract may be dried on a pharmaceutically acceptable carrier, such as maltodextrin or starch.

The plant material of the invention may also be extracted and concentrated without drying to give a liquid extract, which is effective in curbing or suppressing appetite.

A suitable fraction or fractioned extract of a plant used according to the invention may be prepared by one or more of the following process steps:

a) drying and grinding the plant material to a coarse powder;
b) extracting the powder with a solvent to form an extract;
c) fractionating the extract into a number of fractions;
d) concentrating or drying the fractions; and
e) selecting those fractions which are effective in suppressing appetite.

Purified or fractionated extracts may be admixed with any conventional pharmaceutical excipient, diluent or carrier.

The active extract may comprise one or more compounds isolated from the plant used according to the invention, more preferably from the plant *Orbea variegata*, such as saponins, e.g., pregnane glycosides, e.g., stavarosides, more preferably stavarosides A, B, C, D, E, F, G, H, I, J and K. Pregnane glycosides, which can be used in the present invention, include one or more of the following compounds of formula (I) which can be isolated from *Orbea variegate*.

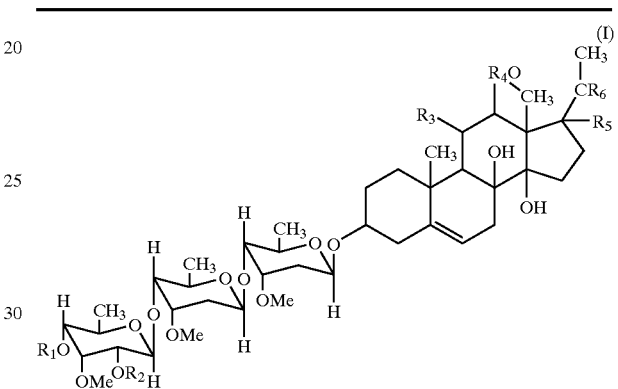

wherein $R_1$–$R_6$ have the following meaning:

| Compound | $R_1$ | $R_2$ | $R_3$ | $R_4$ | $R_5$ | $R_6$ |
|---|---|---|---|---|---|---|
| Stavaroside A | H | H | H | Ang | OH | H, O—Bz |
| Stavaroside B | H | H | H | Ang | OH | H, O—Tig |
| Stavaroside C | H | H | O—Ac | Bz | H | =O |
| Stavaroside D | H | H | O—Ac | Tig | H | =O |
| Stavaroside E | H | H | H | Bz | OH | H, OH |
| Stavaroside F | H | H | O—Ac | Ac | H | =O |
| Stavaroside G | H | H | H | Ac | OH | H, O—Ac |
| Stavaroside H | H | H | OH | H | H | =O |
| Stavaroside I | β-D-glc | H | O—Ang[a] | Bz[a] | H | =O |
| Stavaroside J | β-D-glc | H | O—Ac | Bz | H | =O |
| Stavaroside K | β-D-glc | H | O—Ac | Tig | H | =O |

[a]Interchangeable.
Ac = Acetate
Ang = Angelate
Bz = Benzoate
Tig = Tiglate
β-D-glc = β-D-glucopyranosyl Methods for isolating these pregnane glycosides, e.g., stavarosides, from *Orbea variegata* are known to the person skilled in the art. One such method is described in *Phytochemistry*, Vol. 39, No. 2, pp. 395–403 (1995), said method is hereby incorporated by reference.

The synthesis of such pregnane glycosides, e.g., stavarosides, is state of the art and can, e.g., be carried out by analogous methods as described in WO 98/46243, and incorporated herein by reference in its entirety.

As used herein, the term "active compound" refers to an active compound derived, e.g., isolated, from a plant used according to the invention, e.g., pregnane glycosides of formula (I), derivable, e.g., de novo synthesized compound or synthetic analogue of isolated active compound or any mixtures thereof.

In one aspect, the present invention provides compositions comprising or consisting exclusively or essentially of a plant material of the invention, an extract or an active compound as hereinabove described or any mixtures thereof.

A suitable and accepted in vivo model for measuring appetite suppression or appetite curbing activity in an animal model is described in Example 2. A clinically effective and medically approved anti-obesity drug, sibutramine (REDUCTIL®), can be used as a positive control for reduction in food intake in this model. A plant extract previously reported to have anorectic effects (*Trichocaulon piliferum* (L.f.) N.E.Br.) also tests positive in this in vivo assay, and was used as positive control in Example 2. Positive results from this test model are therefore a very good indicator of clinical efficacy in the human context.

Alternatively, suppression, reduction or curbing of appetite can be assessed by any of the methods referred to in WO 98/46243 and incorporated herein by reference in its entirety.

The compositions of the invention as described hereinabove, may be administered under the supervision of a medical specialist, or may be self-administered.

Daily dosage of a composition of the present invention would usually be single or multiple servings per day, e.g., once or twice daily, e.g., for acute or chronic use. However, benefit may be derived from dosing regimens that may include consumption on a daily, weekly or monthly basis or any combination thereof. Administration of compositions of the invention, e.g., treatment, could continue over a period of days, weeks, months or years, in order, for example, to constantly control the weight, or until a healthy or cosmetically beneficial loss of body weight has occurred. Optimally, the composition of the invention is consumed at least once a day on a regular basis, prior to, i.e., pre- or post-prandial administration or during a meal. Preferably, the compositions of the invention may be consumed prior to a meal.

The composition of the invention may be provided a component of a normal meal, e.g., a nutritional or slimming composition, or dietary supplement, e.g., in the form of a health drink, a snack or a nutritionally fortified beverage, as well as pill, tablet or softgel. When used as a snack or dietary supplement it will preferably be consumed between or before meals.

Alternatively, the composition of the invention may be provided as a meal replacement, e.g., frozen meals or freeze-dried meals.

Optionally, the composition according to the invention may be nutritionally complete, i.e., may include vitamins, minerals, trace elements as well as nitrogen, carbohydrate and fatty acid sources so that it may be used as the sole source of nutrition supplying essentially all the required daily amounts of vitamins, minerals, carbohydrates, fatty acids, proteins and the like. Accordingly, the composition of the invention may be provided in the form of a nutritionally balanced complete meal, e.g., suited for oral or tube feeding.

The composition of the invention may optionally comprise conventional food additives, such as any of emulsifiers, stabilizers, sweeteners, flavorings, coloring agents, preservatives, chelating agents, osmotic agents, buffers or agents for pH adjustment, acidulants, thickeners, texturizers and so on.

Suitable product formats according to the present invention include food and beverage products, e.g., solid food products, like bars, e.g., nutritional bars or cereal bars, powdered drinks, dairy products, breakfast cereals, müesli, candies, confectioneries, cookies, biscuits, crackers, chocolate, chewing-gum, desserts and the like; liquid comestibles, like soft drinks, juice, sports drinks, milk drinks, milkshakes, yogurt drinks or soups, as well as pet treats, pet foods, etc.

It may be desirable to provide the active extract or active compound of the invention as a low calorie meal replacement or other nutritional or slimming product. In this case the meal replacement or other nutritional product is preferably low fat, i.e., less than about 10 en %, or substantially fat-free, i.e., less than about 2.5 en % contributed by fat, such as about 2 en % fat, based on the total caloric content of the composition. Suitably, a single serving of a low calorie meal replacement will have a caloric value of less than about 1000 kcal, and preferably between about 200 kcal and about 500 kcal. Suitable low calorie nutritional or slimming product may include soft drink, such as juice, smoothie or soy-based drink; or dispersed in foods of any sort, such as dairy bars, snacks, soups, breakfast cereals, müesli, candies, tabs, cookies, biscuits, crackers, such as a rice crackers; and dairy products, such as milk-shake and yogurt drink.

In another embodiment of the invention, *Stapelia* or *Orbea biomass*, or the composition as hereinabove described, may conveniently be provided in conjunction with a high protein diet for weight loss purposes or for maintaining a stable body weight, for instance, as an additive to a protein-rich slimming milk shake or other beverage. A high protein diet in this context generally means a minimum of 1.25 g protein/kg body weight/day.

Compositions suitable for incorporating the plant material, extract or active compound of the invention include pharmaceutical compositions, nutraceuticals, nutritional compositions, such as dietary supplements, slimming compositions, medical nutrition or functional food. In addition to the plant material, extract or active compound of the invention, the composition of the invention may contain at least one pharmaceutically or nutritionally acceptable carrier. Suitable delivery vehicles include sachets, soft gel, powders, syrups, pills, capsules, tablets, inhalants, implants, liquid drops, sublinguals, injectables, patches, suppositories, liquids, etc.

The amount and dosage regimen of the composition of the invention to be administered is determined in the light of various relevant factors including the purpose of administration, the age, sex and body weight of individual subject, i.e., inter alia on the severity of the subject's obesity or overweight.

Preferred delivery formats for the appetite suppressing or appetite curbing composition of the invention, would be as a dietary supplement comprising about 5 mg to about 1000 mg, preferably about 10 mg to about 500 mg dry weight dosage of a *Stapelia* and/or *Orbea* extract, e.g., as pill, tablet or softgel, or comprising about 0.1 wt % to about 10 wt %, preferably about 0.1 wt % to about 5 wt %, more preferably about 0.5 wt % to about 5 wt % of a *Stapelia* and/or *Orbea* extract, e.g., as a nutritionally fortified beverage, bar or soft chew. A typical dosage of active compounds of the invention is about 0.01 mg body weight/day to about 200 mg/kg body weight/day, preferably about 5 mg/kg body weight/day to about 100 mg/kg body weight/day.

An appropriate dosage range would be approximately 100 mg–100 g/kg body weight/day, expressed in terms of dry weight of the source plant material (biomass). A suitable daily dosage for an average, e.g., 70 kg, human being is optimally in the range of about 1 g to about 100 g, preferably of about 5 g to about 80 g, and even more preferably of about 10 g to about 50 g. A typical consumption extracted material, e.g., that recovered from a first ethanolic extraction step, would be about 100 mg dry weight/person/day to about 10 g dry weight/person/day, or about 1 mg dry weight/kg/day to about 200 mg dry weight/kg/day, preferably about 3 mg/kg/day to about 125 mg/kg/day. In terms of purified bioactive compound isolated from *Stapelia* and/or *Orbea*, synthetic analogue thereof or de novo synthesized compound, a suitable dosage range is about 0.01 mg/kg to about 100 mg/kg body weight/day, preferably about 0.05 mg/kg/day to about 10 mg/kg/day. In one aspect of the invention, a suitable dosage range of the active compound is about 0.1 mg/day to about 2 g/day.

Preferred methods of administration of the compositions of the invention would be by any enteral route, e.g., oral, parenterally, e.g., intravenously, topically, e.g., through use of a skin patch, by delayed-release mechanisms, e.g., through an implant or patch, or across mucous membranes, e.g., by sublinguals or as a suppository.

Oral pharmaceutical or dietary supplement forms may be made by conventional compounding procedures known in the pharmaceutical art, that is, by mixing the active compound of the invention together with edible pharmaceutically acceptable solid or liquid carriers and/or excipients, e.g., fillers, such as cellulose, lactose, sucrose, mannitol, sorbitol, and calcium phosphates; and binders, such as starch, gelatin, tragacanth, methylcellulose and/or polyvinylpyrrolidone (PVP). Optional additives include lubricants and flow conditioners, e.g., silicic acid, silicon dioxide, talc, stearic acid, magnesium/calcium stearates and polyethylene glycol (PEG) diluents; disintegrating agents, e.g., starch, carboxymethyl starch, cross-linked PVP, agar, alginic acid and alginates, coloring agents, flavoring agents and melting agents. Dyes or pigments may be added to the tablets or dragée coatings, for example, for identification purposes or to indicate different doses of active ingredient.

In addition to the plant material or active compound of the invention, the composition of the invention may include one or more further active ingredients selected from the following: capsaicine (red pepper); fatty acids, especially linoleic acid (LA) and conjugated linoleic acid (CLA); glycomacropeptide (GMP); Long Chain Triglyceride (LCT); enterostatin; galactose; glucuronic acid; fibers such as pectin, guar gum, incl. partially hydrolysed guar gum, psyllium and β glucan; hydroxycitrate (HCA); citrus; guarana; β hydroxy butyrate; medium chain tryglycerides (MCTs); D-tagatose; *Ephedra* L., including Ma Huang or *Ephedra sinica* Riedl.; ephedrine; caffeine; potato extract; green tea extract; epigallocatechin gallate, or other catechins; peptide D4; vitamins B, C and/or E; and chromium picolinate. Alternatively, the active extract or active compound of the invention may be combined with anti-obesity drug, such as sibutramine (REDUCTIL®), or with another plant extract having anorectic effects, such as *Trichocaulon piliferum* (L.f.) N.E.Br. For example, the composition of the invention may be provided in the form of a kit for separate, sequential or simultaneous administration in conjunction with anti-obesity drug.

In another aspect of the invention, there is provided a combined pharmaceutical preparation for simultaneous, separate or sequential use for the treatment of obesity or overweight comprising active extract or active compound of the invention and one or more drug(s) for suppressing or curbing appetite.

EXAMPLES

Example 1

Preparation of Plant Extracts

Taxonomically identified plant biomass (stems) is freeze-dried and ground to a fine powder using a coffee grinder or equivalent.

Extraction procedure: 100 mL of ethanol are added to 10 g of plant powder and stirred at room temperature for 15 hours. Each sample is filtered and the extract concentrated to dryness under vacuum. A 250 mg sample is used for testing in a rat satiety model.

A sap (juice) sample is prepared by taking the whole plant material and pressing to remove the sap (juice) from the biomass. The sap is then freeze-dried to produce a sample for testing in a rat satiety model.

Example 2

Testing of Plant Extracts

Animals: These studies are conducted with male Sprague-Dawley rats (RA238 strain OFA/IC; IFFA-CREDO, l'Arbresle, Cedex, France). At the time of arrival the animals weigh 270–290 g and are housed in groups of 5 in Macrolone type IV cages prior to the experiment. The animals are maintained under a 12:12 light dark cycle (lights off at 18:00) in a temperature and humidity controlled environment (21–23° C.; 47% humidity). Three days before the start of an experiment, the animals are weighed and individually housed in Macrolone type IIIA cages and transferred into the room with the recording devices, which is equally controlled for temperature and humidity and in which no other animals are housed. Normal rat chow pellets (Nafag Ecosan 890, Gossau, Switzerland) and tap water are present ad libitum and are provided by modified food troughs and drinking spouts, which allow continuous recording of the food consumed.

Measurement of food intake: The custom made TSE-software Drink/Feed (version 2.16) allows continuous registration of food intake. Food intake is recorded by continuously weighing the amount of food remaining in a round stainless steel food basket (8 cm in diameter), which offers food pellets to the animals at a similar position as the original food troughs.

Food intake is continuously recorded in 1-hour intervals over the entire time of an experiment (90–94 hours). A typical experiment starts on Monday at 10 a.m. with a 2-day run-in phase and lasts until Friday 6 a.m. (92 hours), i.e., at the end of the dark phase of 4 consecutive days. Plant extract test substance application is typically performed on Wednesday, 2 hours before the onset of the third dark phase.

Experimental design: The following experiments are performed: The animals are randomly assigned to groups of 6, which receive either vehicle (10% Tween 80 in water ad inj. 5 mL/kg) or plant extract dissolved in vehicle (100 mg/kg). After a 2-day, run-in phase, plant extracts are applied 2 hours before the dark phase of the third light-dark cycle. For exact dosing, the weight of each animal is determined on the day of the experiment and recorded, together with any unusual observations, e.g., stressed animals, difficulties with plant extract application, etc.

Data Analysis: Data are presented as mean±SEM. Food intake is displayed cumulatively in 24-hour time intervals to allow easy visualisation of ingestive behavior over an entire circadian cycle and to allow best comparison with previously published data. Statistical analysis to detect differences in ingestive behavior between the control group and the treatment group is performed by 2 way analysis of variance with repeated measures followed by a Bonferroni correction (RM-ANOVA, Bonferroni; SigmaStat). Three hypotheses are tested by RM-ANOVA: (a) are the time courses parallel or do they differ in any way over time?; (b) if curves are parallel, is there a difference by a shift of a constant level?; and (c) do the curves remain at the same level over time? The time interval for the statistical analysis of the data comprised 14 hours, i.e., covering the entire dark phase (12 hours) after drug application, which occurred 2 hours before dark onset. The main differences in food intake are to be expected during this time period. Extending the statistical calculations to 24 hours would make the analysis less sensitive, because during the additional 10 time points the animals are usually asleep. P values less than 0.05 were considered to indicate statistically significant differences. *indicates differences at p<0.05; indicate differences at p<0.01; * indicate differences at p<0.001.

Results: The results of the appetite suppressing activity are shown in Table 1. *Trichocaulon piliferum* had been previously described (WO 98/46243) to have appetite suppressing activity and served as positive control. It can be seen that extracts of *Stapelia gigantea* and *Orbea variegata* show appetite suppressing activity for up to 14 hours after administration of the plant extract. Also the sap of *Stapelia gigantea* shows appetite suppressing activity for up to 8 hours after administration of the dried sap. The activity is not dependent on the mode of administration (PO or IP). Plants of the genera *Ceropegia* L., *Rhytidocaulon* P. R. O Bally, *Tromotriche* Haw. and Sarcostemma R.Br. which belong to the same family Asclepiadaceae showed no appetite suppressing activity.

TABLE 1

In Vivo Appetite Suppressant Activity of Asclepiadaceae

| Species | Administration | Activity at 100 mg/kg |
|---|---|---|
| *Trichocaulon piliferum* | PO | ***After 14 hours |
| *Ceropegia stapeliiformis* Haw. | PO | Inactive |
| *Ceropegia aristolochioides* Dcne. | PO | Inactive |
| *Cyanchum nodosum* (Jum.&H.Perr.) Desc | PO | Inactive |
| *Ceropegia woodii* Schltr. | | Inactive |
| *Rhytidocaulon macrolobum* Lavranos | PO | Inactive |
| *Stapelia gigantea* | PO | ***After 14 hours |

TABLE 1-continued

In Vivo Appetite Suppressant Activity of Asclepiadaceae

| Species | Administration | Activity at 100 mg/kg |
|---|---|---|
| *Stapelia gigantea* | IP | ***After 14 hours |
| *Stapelia gigantea* (sap) | PO | ***After 8 hours |
| *Orbea variegata* | PO | ***After 14 hours |
| *Tromotriche engleriana* (Schltr.) Leach | PO | Inactive |
| *Sarcostemma socotranum* Lavranos | PO | Inactive |

***p < 0.001

What is claimed is:

1. A method of suppressing appetite in a mammal in need thereof which comprises administering to said mammal a therapeutically effective amount of a plant material from a plant of the genus *Stapelia* or *Orbea*.

2. A method of controlling obesity in a mammal in need thereof which comprises administering to said mammal a therapeutically effective amount of a plant material from a plant of the genus *Stapelia* or *Orbea*.

3. A method of promoting weight loss or maintenance of a desired body weight in a mammal in need thereof which comprises comprises administering to said mammal a therapeutically effective amount of a plant material from a plant of the genus *Stapelia* or *Orbea*.

4. The method of claim 1, wherein said plant is *Stapelia gigantea* or *Orbea variegata*.

5. The method of claim 1, wherein said plant material is sap, a concentrate, an extract, a fraction or an active compound from said plant.

6. The method of claim 1, wherein said plant material comprises a therapeutically effective amount of at least one saponin.

7. The method of claim 1, wherein said plant material comprises a therapeutically effective amount of a stavaroside, wherein said stavaroside is stavaroside A, stavaroside B or stavaroside C.

8. The method of claim 7, wherein stavaroside is stavaroside C.

9. The method of claim 5, wherein said plant material is derived from a process comprising treating said plant material with an alcohol-based solvent.

10. The method of claim 9, wherein said alcohol based solvent is ethanol.

* * * * *